United States Patent [19]

Ruszala et al.

[11] 4,205,386
[45] May 27, 1980

[54] ELECTROCARDIOGRAPHIC AND BLOOD PRESSURE WAVEFORM SIMULATOR DEVICE

[75] Inventors: Frederick B. Ruszala, Sterling Heights; Kenneth J. Cook, Troy, both of Mich.

[73] Assignee: The Valeron Corporation, Oak Park, Mich.

[21] Appl. No.: 938,430

[22] Filed: Aug. 31, 1978

Related U.S. Application Data

[63] Continuation-in-part of Ser. No. 882,357, Mar. 1, 1978, Pat. No. 4,204,261.

[51] Int. Cl.² ............... G06G 7/26; G06J 1/00; H01C 10/46
[52] U.S. Cl. .......................... 364/607; 328/185; 338/220; 339/147 R; 364/578; 364/851
[58] Field of Search ............ 364/607, 608, 824, 825; 328/14, 187, 228, 185; 339/147 R; 338/220, 221

[56] References Cited

U.S. PATENT DOCUMENTS

| | | | |
|---|---|---|---|
| 3,323,068 | 5/1967 | Woods | 328/187 |
| 3,384,981 | 5/1968 | Baessler et al. | 35/17 |
| 3,448,323 | 6/1969 | Owens | 339/147 R |
| 3,500,213 | 3/1970 | Ameau | 328/14 |
| 3,552,036 | 1/1971 | Mahler | 35/17 |
| 3,629,662 | 12/1971 | Cattey et al. | 338/220 |
| 3,641,442 | 2/1972 | Boucher | 328/187 |
| 3,728,587 | 4/1973 | Offerman | 339/147 R |
| 3,736,363 | 5/1973 | Baessler et al. | 328/187 |
| 3,748,532 | 7/1973 | Rosenbaum | 338/220 |
| 3,793,589 | 2/1974 | Puckette | 364/608 |
| 3,835,403 | 9/1974 | Leineman | 328/14 |
| 3,838,414 | 9/1974 | Wiles | 328/14 |
| 3,908,178 | 9/1975 | Johnson et al. | 338/221 |
| 3,938,051 | 2/1976 | Eisenberg | 328/187 |
| 4,001,555 | 1/1977 | Levis et al. | 364/608 |
| 4,061,909 | 12/1977 | Bryant | 328/14 |

Primary Examiner—Felix D. Gruber
Attorney, Agent, or Firm—Krass & Young

[57] ABSTRACT

Apparatus for simulating waveforms utilized to check the operability of a remote display device. The apparatus includes a waveform generator for providing electrical signals representing simulated waveforms. An interface circuit for coupling the waveforms to the remote display device includes a bridge network having a plurality of resistive legs in which a variable resistance element is provided in one of the legs. The variable resistance element is coupled to the waveform generator. An excitation signal from the remote display device is coupled to an input of the bridge. The electrical signals from the generator causes the resistance of the variable resistance element to correspondingly vary and provide simulated waveforms at the output of the bridge network to the remote display device. According to another aspect of this invention, the device simulates both electrocardiographic and blood pressure waveforms, with the beginning of the blood pressure waveform being delayed from the beginning of the electrocardiographic waveform so that the waves are provided in a timed sequence corresponding to waveforms that would ordinarily be supplied by a live patient. An interconnection device is also supplied for coupling the simulator device to a blood pressure monitor, with the interconnection device automatically compensating for signal variations between a variety of blood pressure monitors so that the simulator device can be universally employed.

25 Claims, 11 Drawing Figures

ELECTROCARDIOGRAPHIC AND BLOOD PRESSURE WAVEFORM SIMULATOR DEVICE

CROSS REFERENCE TO RELATED APPLICATION

This application is a continuation-in-part of U.S. Ser. No. 882,357, filed Mar. 1, 1978, now U.S. Pat. No. 4,204,261 entitled "Complex Analog Signal Generator" having the same inventors and assignee as the present invention.

BACKGROUND OF THE INVENTION

This invention relates to an electronic circuit for generating complex time-varying analog signal waveforms. More particularly, it involves apparatus for simulating electrocardiographic and/or blood pressure waveforms which can be utilized to test remote display devices.

In the above-described application, there is disclosed electronic circuitry for generating time-varying analog signals, preferably representing electrocardiographic and blood pressure waveforms. These waveforms can be coupled to remote display devices to check their operability. A blood pressure monitor, when in actual use, monitors electrical waveforms derived from a transducer sensing the blood pressure of a live patient. The blood pressure monitor provides an excitation signal to the transducer in order to initially energize the transducer. However, different types of blood pressure monitors provide different types of excitation signals, these signals usually being of the pulsed, direct current (DC) or alternating current (AC) type. A simulator device must utilize the excitation signal from the blood pressure monitor. In the above-referenced copending application, there is provided two separate interface circuits, one for a DC excitation signal and one for an AC excitation signal. Unfortunately, this necessitates increased costs for a user who has different types of blood pressure monitors to be checked. For example, a hospital may carry a wide variety of blood pressure monitors which have different types of excitation signals.

In checking the operability of the remote display devices, it is advantageous for the simulator device to simulate waveforms which closely represent the waveforms that would ordinarily be supplied by a live patient. Under true operating conditions, where the patient is being simultaneously monitored by an electrocardiogram machine and a blood pressure monitor, the blood pressure waveform will appear delayed from the electrocardiographic waveform. However, the simulator device of the parent application initiated both simulated waveforms at the same time. While this has provided reliable means for checking the operability of the displays, it would be further advantageous to provide these waveforms in a timed sequence corresponding to the waveforms actually provided by a live patient.

As noted above, it would be advantageous to provide a universal simulator device which is compatible with a wide variety of blood pressure monitors. According to another aspect of this invention, there is provided an interconnection cable which is specifically designed for use with a particular blood pressure monitor. Since each monitor may utilize a particular type of transducer and supply a certain type of excitation signal, complex modifications had heretofore been necessary to make the particular monitor signals compatible with that of a simulator device. To overcome this problem, the interconnection device of the present invention is specifically designed for the particular blood pressure monitor being utilized so as to make its signals compatible with the simulator device. Therefore, the same simulator device can be utilized in conjunction with a variety of different blood pressure monitors merely by changing the cable specifically designed for the monitor under test.

OBJECTS AND SUMMARY OF THE INVENTION

Therefore, it is an object of the invention to provide a waveform simulator which is compatible with a variety of remote display devices having different types of excitation signals.

It is another object of the present invention to provide simulated electrocardiographic and blood pressure waveforms in a timed sequence corresponding to those waveforms which would be derived from a live patient.

A further object of this invention is to provide an interconnection device which permits the same waveform simulator to be utilized with a variety of different remote display devices.

These and other objects of this invention are accomplished by providing an apparatus which includes a waveform generator for providing electrical signals representing simulated waveforms. An interface circuit for the apparatus includes a bridge network having a plurality of resistive legs, with a variable resistance element in one of the legs. The variable resistance element is coupled to the signal generator. The excitation signal from the remote display device under test is coupled across an input of the bridge. The electrical signals from the generator causes the resistance of said variable resistance element to correspondingly vary and provide said simulated waveforms to the remote display at the output of the bridge network. Accordingly, either AC, DC or pulsed excitation signals can be utilized with the simulator apparatus.

According to another aspect of the invention, the apparatus supplies both electrocardiographic and blood pressure simulated waveforms which can be utilized to check the operability of an electrocardiogram machine and a blood pressure monitor, respectively. The apparatus includes a first generator for providing simulated electrocardiographic waveforms and a second generator for providing simulated blood pressure waveforms. Means are provided for delaying the initiation of the blood pressure waveform for a predetermined period of time so that the electrocardiographic and blood pressure waveforms are provided in a timed sequence corresponding to waveforms that would ordinarily be supplied by a live patient.

Still another aspect of this invention is the provision of an interconnection device for coupling a blood pressure monitor to the simulator device. The interconnection device is preferably in the form of a cable having a plurality of conductors therein and terminating in connectors on either end of the cable. A plurality of resistors are contained within one of the connectors and have a common node coupled to one of the conductors for supplying the excitation signal from the blood pressure monitor. The other end of the resistors are each attached to separate terminals in one of the connectors to provide alternative conductive paths which may be selectively coupled to the simulator device to modify its output signal. The value of the resistors are chosen according to the particular characteristics of the blood pressure monitor being tested.

BRIEF DESCRIPTION OF THE DRAWINGS

These and other objects and advantages of this invention will become apparent upon reading the following specification and by reference to the accompanying drawing in which.

FIG. is a front plan view of the waveform simulator device of the present invention.

DESCRIPTION OF THE PREFERRED EMBODIMENTS

A. General Description

Figure 1:
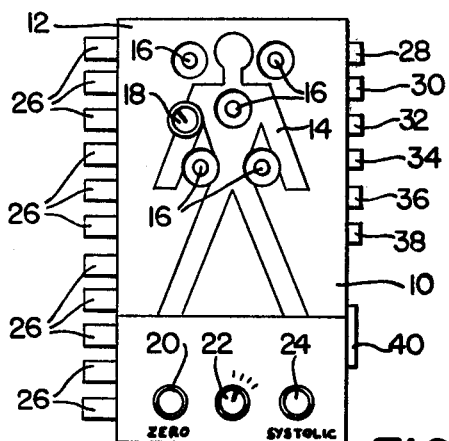
Figure 2:
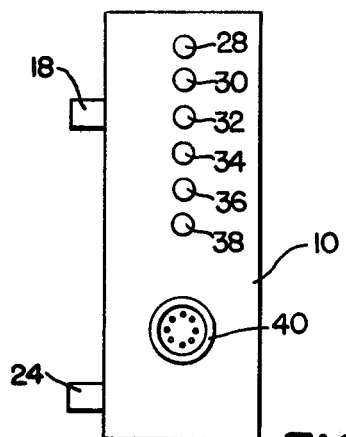
FIG. 2 is a right side plan view of the device shown in FIG. 1.

Referring to FIGS. 1 and 2 of the drawing there is shown a substantially rectangular box defining a housing for the simulator device 10 of the present invention. A front plate 12 includes a pictoral representation of a patient 14 and a plurality of snap-type connectors 16 disposed relative to patient 14 for receiving disposable type electrode cables from an electrocardiogram machine being tested. A plurality of knobs 18 and 20, 22, and 24 are coupled to particular components in the electrical circuitry internally contained by the housing. A series of jacks 26 on one side panel of the housing provide connections to electrocardiogram machine patient cables and may be color-coded to designate the connections as defined by the terminology adopted by the American College of Cardiology. An opposite side panel of the device 10 includes six pushbutton switches 28-38 and a nine socket receptacle 40 which are utilized when testing a blood pressure monitor as will be more fully discussed herein. Upon inspection of FIGS. 1 and 2, it will be seen that the simulator device 10 of the present invention provides a compact tool which provides both simulated electrocardiographic waveforms via jacks 28 and simulated blood pressure waveforms via receptacle 40, which waveforms are advantageously utilized to check the operability of remote display units such as an electrocardiogram machine and a blood pressure monitor which are normally utilized to sense the physical characteristics of a live patient.

Figure 3:
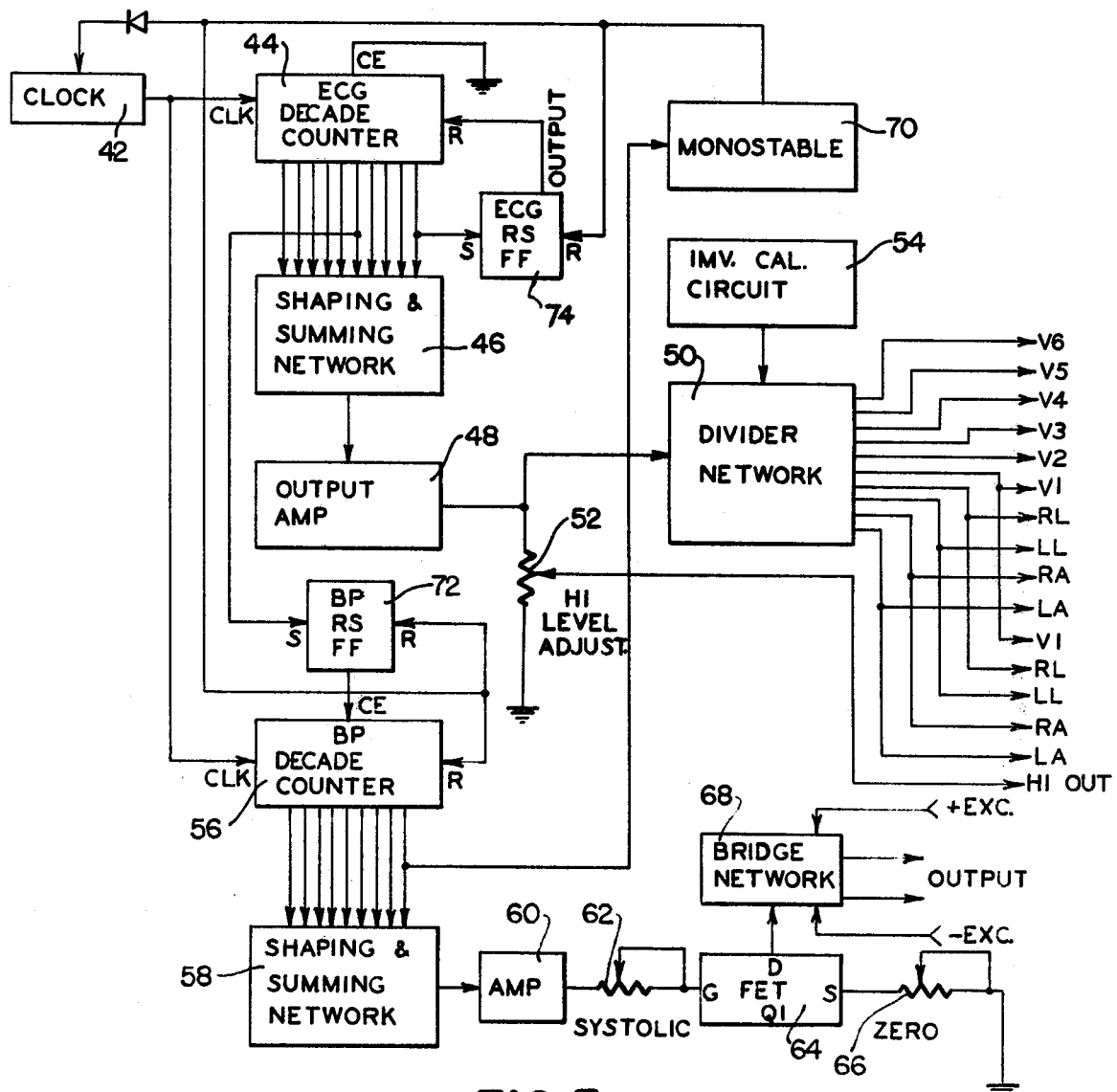
FIG. 3 is a block diagram showing the major components of the circuitry of the present invention.

The block diagram shown in FIG. 3 illustrates the major components of the electrical circuitry of the present invention. When the circuit is energized a clock circuit 42 generates a plurality of clock pulses which are fed to a first decade counter 44 which has a plurality of output stages represented by the lines emanating from the lower portion of counter 44. The clock pulses cause the counter 44 to count, thereby causing the output stages to successively change from a low state to a high state and back to the low state during a specific time period.

Particular output stages of counter 44 are connected to a first shaping and summing network 46. Network 46 shapes the particular outputs of counter 44 to form particular segments of an electrocardiographic waveform. Network 46 then sums these segments to produce the complete waveform. The output of network 46 is coupled to amplifier 48 whereat the complete waveform is amplified.

The output of amplifier 48 is coupled to a divider network 50 that divides the waveform into a plurality of outputs having different amplitudes and to a potentiometer 52 for adjusting the high level output. A calibration circuit 54 provides a one millivolt reference signal which is fed to divider 50. The reference signal is used for checking the gain of a display device such as an electrocardiogram machine to which divider network 50 may be connected, for example, via jacks 26 shown in FIG. 1.

Clock pulses from clock circuit 42 are also connected to a second decade counter 56 having a similar number of output stages and operating in the same manner as counter 44. Particular output stages of counter 56 are coupled to a second shaping and summing network 58. Network 58 shapes particular output stage signals from counter 58 to provide a simulated blood pressure signal segments which are then summed to provide a complete waveform. It should be noted that the circuit elements so far described in connection with FIG. 3 are more fully explained in the above referenced copending application. Consequently, these elements will only be discussed in such detail so that a full understanding of the claimed subject matter of the present invention can be readily understood.

The output of network 58 is coupled to an amplifier 60 where the completed waveform is amplified. A potentiometer 62 which is manually adjustable by knob 24 of FIG. 1 regulates the amplitude of the blood pressure waveform to set the desired systolic level. The output of potentiometer 62 is coupled to a current regulator such as a transistor. In the preferred embodiment, the output of potentiometer 62 is coupled to the gate of a field effect transistor 64 whose source region is coupled to another potentiometer 66 for initially zeroing the output of the simulator device 10 when coupled to a blood pressure monitor as will be more fully discussed herein. The drain region of transistor 64 is coupled to a bridge network 68 to which an excitation signal is supplied from the blood pressure monitor under test. It is the feature of this invention that bridge network 68 makes the simulator device of the present invention compatible with a variety of different blood pressure monitors which may supply correspondingly varied types of excitation signals. Regardless of the type of excitation signal from the blood pressure monitor, the output of the bridge network 68 will provide a simulated blood pressure waveform which can be utilized to check the operability of the particular monitor under test.

Pursuant to the present invention, provision is also made for simultaneously supplying electrocardiographic and blood pressure waveforms in a timed sequence which correspond to the timed sequence of such waveforms which would be supplied by a live patient.

This is accomplished by the unique interaction of monostable circuit 70, a first flip-flop 72 coupled to blood pressure counter 56, and a second flip-flop 74 coupled to electrocardiographic waveform counter 44. First flip-flop 72 is of the RS-type including set and reset inputs, and an output. The output is coupled to an enabling input (CE) of counter 56. An intermediate stage of counter 44 is coupled to the set input of flip-flop 72. The last stage of counter 56 is coupled to an input of monostable circuit 70. In the preferred embodiment monostable circuit 70 is a one shot multi-vibrator which provides a HIGH output pulse of a given pulse width upon receipt of a triggering pulse at its input. The output of monostable 70 is coupled to the reset input of flip-flop 74 which is also of an RS-type, as well as to the reset input of both flip-flop 72 and counter 56, and to a disabling input of clock circuit 42. As will be discussed below, the setting of blood pressure flip-flop 72 by an intermediate stage of electrocardiogram counter 44 causes a delay in the initiation of the blood pressure waveform with respect to the beginning of the electrocardiographic waveform. The width of the output pulse from monostable 70 determines the period between successive waveforms. According to another aspect of this invention, means are provided via knob 22 of FIG. 1 to vary the output pulse width from monostable 70 such that the blood pressure waveform corresponds selectively to either 120, 90 or 60 beats per minute.

B. Detailed Description

Figure 4A:
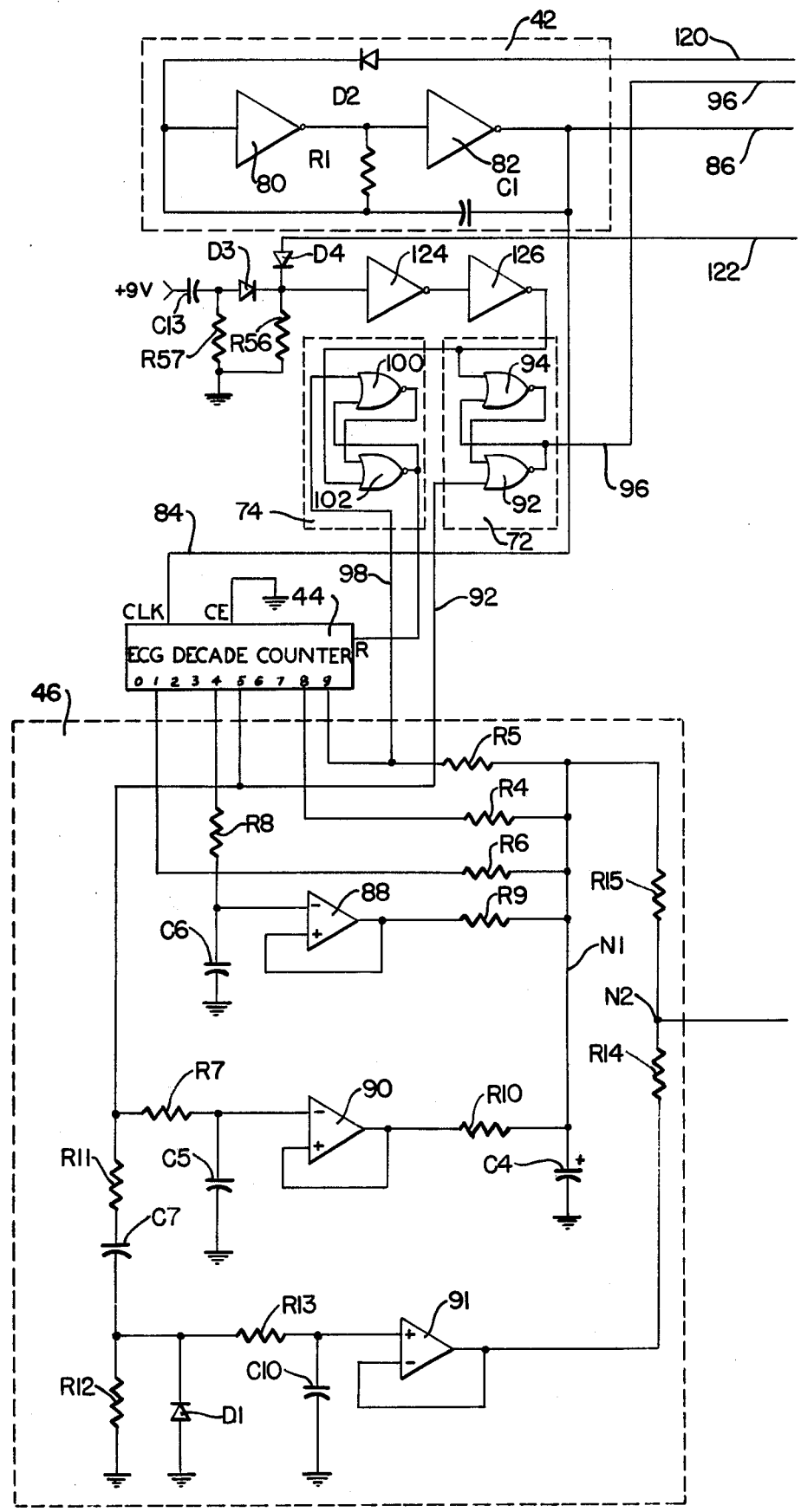
FIGS. 4A-4C comprise a schematic diagram showing the circuitry of FIG. 3 in more detail.
Figure 4B:
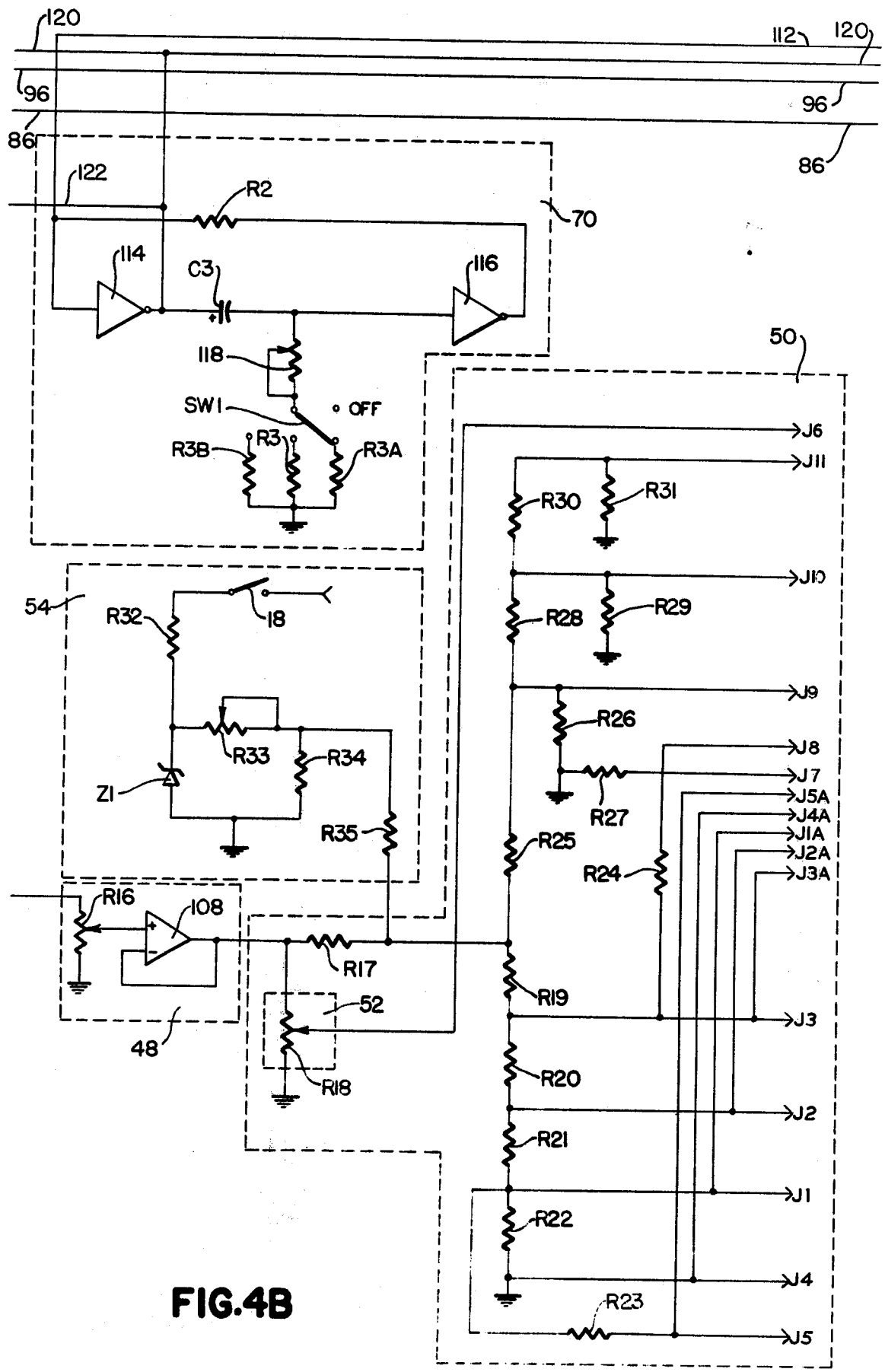
Figure 4C:
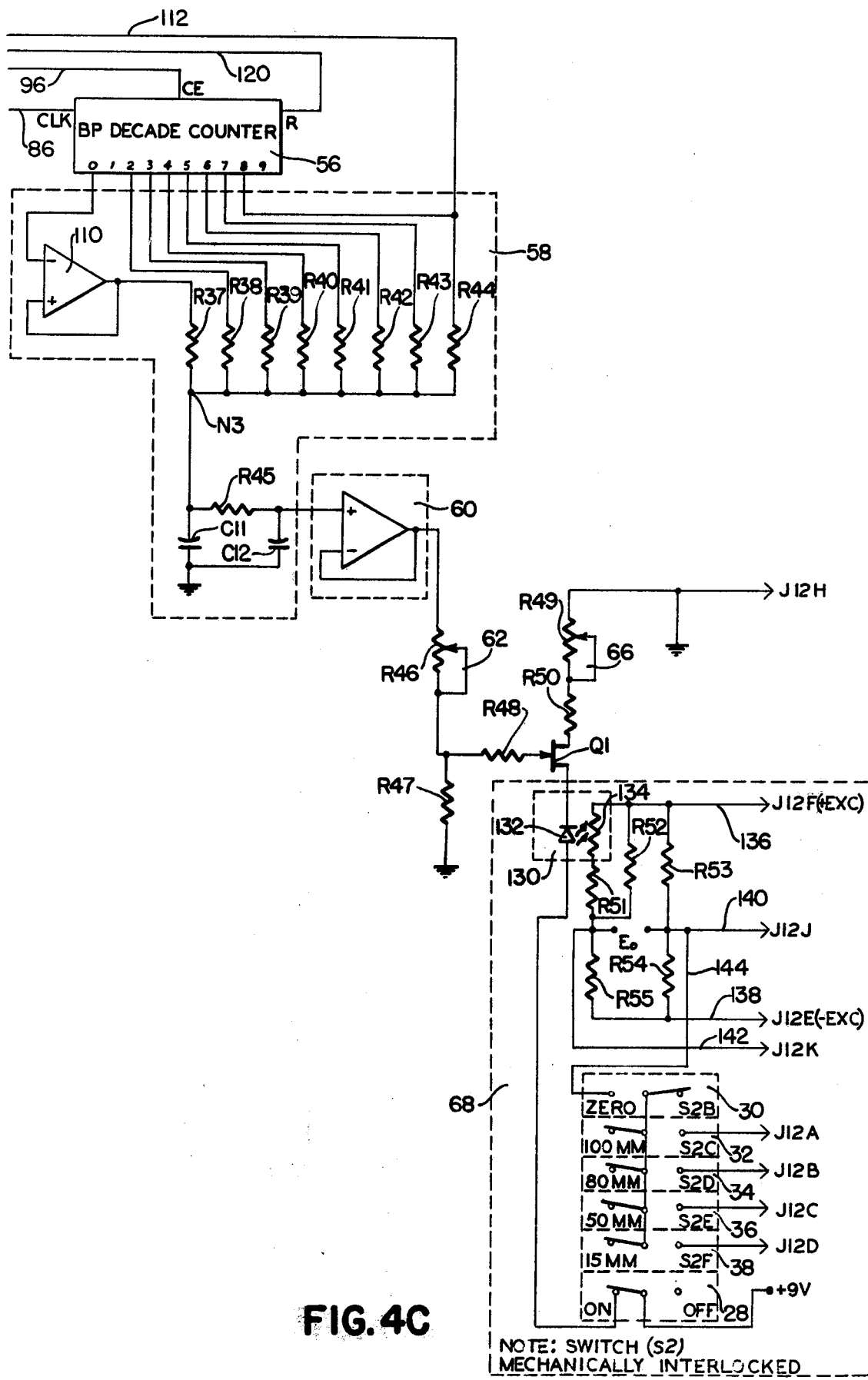

The components illustrated in block diagram form in FIG. 3 are shown in more detail in FIG. 4. The details of some of the components are encompassed by dotted lines in FIG. 4 to help the reader in ascertaining the connection between the various components.

Clock 42 employs a pair of inverting amplifiers 80 and 82, with the output of amplifier 80 connected to the junction of the input of the amplifier 82 and a resistor R1. A resistive-capacitive circuit consisting of resistor R1 and capacitor C1 determines the frequency of clock 44. The output of clock 42 is coupled to the clock inputs of counters 44 and 56 via lines 84 and 86, respectively.

The output stages of counter 44 are labelled in this embodiment by the numerals 0-9 on the bottom portion of the block in the drawing. In this embodiment, only stages 1, 4, 5, 8, and 9 are utilized to initiate the shaping and summing network 46 which provides the electrocardiographic waveform. The shaping and summing network 46 is described in more detail in the above referenced application. Briefly, the P segment of the electrocardiographic waveform is obtained from the first period or stage counter 44 by summing this signal through resistor R6 to a common node N1. To derive the Q waveform segment, counter stage 4 is utilized. Since the Q wave is a negative going wave and of different rise time than the P wave, the output of the stage 4 is coupled to a shaping circuit comprised of R8 and C6. This shaped waveform is then inverted by buffer 88 and then summed at node N1 through resistor R9.

Stage 5 is utilized to generate both the R and S electrocardiographic waveform segments. The S segment, like the Q segment, is a negative going waveform. The S wave is derived by shaping the output from stage 5 by resistor R7 and C5, then inverting the wave by buffer 90 and finally summing this shaped signal through resistor R10 at node N1.

The output of stage 5 of counter 44 is also coupled to the set input of flip-flop 72 via line 92. Flip-flop 72 is comprised of two cross-coupled NOR gates 94 and 96 to form an RS-type flip-flop known in the art. The output of flip-flop 72 is coupled via line 96 to the enabling input (CE) of blood pressure counter 56.

The T segment of the electrocardiographic waveform is of a longer duration than any of the other segments and therefore both stages 8 and 9 are utilized from counter 44. Stage 8 is coupled to summing junction N1 through resistor R4 and stage 9 is coupled to node N1 through resistor R5. The falling edge of the output of the stage 9 is utilized to set flip-flop 74 via line 98. Flip-flop 74 is similarly an RS-type flip-flop comprised of cross-coupled NOR gates 100 and 102. Flip-flop 74 and 72 can be of a variety of known flip-flops. In this example, they are commercially available as a pair on one integrated circuit component from Motorola as Componet No. MC14001. As will be further described herein the falling edge of stage 9 of counter 44 is used to set flip-flop 74 and disable counter 44 while blood pressure counter 56 times out in order to give the electrocardiographic and blood pressure waveforms the proper timing relationship.

The R waveform segment has steep rising and falling edges. This is obtained by using the output of counter 44 stage 5 and differentiating it through capacitor C7 and resistor R12, with diode D1 causing capacitor C7 to recover quickly. Resistors R13 and capacitor C10 are used for shaping the wave, with buffer 91 and resistor R14 presenting the waveform at node N2. The P, Q, S, and T waveforms are summed at node N1, with this combined waveform being further summed with the R waveform segment at node N2 to provide the completed electrocardiographic waveform.

The completed electrocardiographic waveform is coupled to output amplifier 48 through an internally adjustable potentiometer R16 which is adjusted to provide the correct output level to the display under test. Amplifier 48 consists of a buffer amplifier 108 such as an LM324 integrated circuit having a feedback line coupled to its inverting input. The output of amplifier 48 is coupled to one side of potentiometer 52 which is adjustable by the user. Resistors R17 and R19 through resistor R31 form a divider network where the electrocardiographic signal is tapped off, to be fed to the differential inputs of the remote display under test. Since all electrocardiographic monitors have a 1000:1 amplifier, resistor R16 is adjusted so that the RA to LA outputs provides a 1 millivolt output which, in turn, gives a rading of 1 volt on the electrocardiogram display.

The divider network 50 employs a parallel-series combination of resistors to divide the signal from the output of amplifier 48 into a plurality of outputs at jacks 26 which are color coded to provide the simulated electrocardiographic waveform with different amplitudes depending upon which jacks are connected to the display under test. A one millivolt output switch such as knob switch 18 shown in FIG. 1 is utilized to provide a 1 millivolt output across jacks labelled J1 and J2 when depressed. Potentiometer R33 of calibration circuit 54 is adjusted to provide this one millivolt output. Potentiometer R18 is adjusted to provide the high level output taken across jacks J6 and J4A. The outputs labelled J1-J5 provide the electrode connections 16 on front panel 12 of device 10 shown in FIG. 1. The jacks labelled J1A-J5A and J7-J11 in FIG. 4 corespond to the jacks 26 located on the side of the device housing.

As noted above, the same clock frequency is utilized to drive blood pressure decade counter 56. However, counter 56 is initiated after the initiation of electrocardiogram counter 44 since its enabling input is coupled to an intermediate stage (here, stage 5) of counter 44 via line 96. The blood pressure waveform is one continuous waveform. Accordingly, almost all of the output stages of counter 56 are utilized. To achieve a rounding leading edge of the waveform, buffer amplifier 110 has its input coupled to the 0 stage of counter 56 and its output coupled to a summing node N3 through resistor R37. Stages 2 through 8 are coupled to node N3 through resistors R38–R44, respectively. Stage 8 of counter 56 is coupled via line 112 to monostable circuit 70 through capacitor C2. When stage 8 is activated, it provides a trigger pulse to monostable circuit 70 which in turn provides an output pulse of a predetermined pulse width. Monostable 70 includes 2 inverting amplifiers 114 and 116 which are connected together via capacitor C3. The width of the output pulse of monostable 70 is determined by the RC network comprised of capacitor C3 and the resistive network defined by potentiometer 118 which is series connected with either of resistors R3, R3A, or R3B through a four position switch SW1 such as switch 22 of FIG. 1. Resistors R3, R3A, and R3B provide monostable 70 with an output pulse width of varying widths to define the periods between the electrocardiographic and blood pressure waveforms. According to a feature of this invention, resistors R3, R3A and R3B define a blood pressure waveform having a frequency corresponding to 90, 60 and 120 beats per minute, respectively. The output of monostable 70 is coupled to the reset input of blood pressure counter 56 via line 120. Counters 44 and 56 are commercially available from Motorola, Inc as Component No. MC14017B. As it is known in the art, when such counters have a HIGH level applied at their reset input, the counter is disabled and will not count. Similarly, the output of monostable 70 is coupled to the reset input of flip-flop 72 and 74 via line 122 through diode D4 and inverters 124 and 126. Capacitor C13, resistor R57 and diode D3 cause a pulse to be generated when the simulator device is initially turned on to insure that the flip-flops 72, 74 are reset. The output of monostable 70 is also coupled to clock circuit 42 through diode D2 which holds the clock circuit 42 in a disabled state for the duration of the monostable output pulse.

The electrical signals from the output stages of blood pressure counter 56 are summed at summing junction N3. These signals are then shaped, first by capacitor C11, and then by the RC network comprised of resistor R45 and capacitor C12. The completed blood pressure waveform is then presented to the noninverting input of buffer amplifier 60 where it is amplified. The output of amplifier 60 is coupled to a fine adjustment potentiometer 62 which is manually adjustable by the customer via knob 24 of FIG. 1 to adjust the amplitude of the blood pressure waveform. The varying analog signal biases the gate of field effect transistor Q1 through the divider network consisting of resistor R47 and R48. Resistor R50 and potentiometer 56, which is manually adjustable via knob 20 of FIG. 1, adjusts the current through the light emitting diode (LED) portion of photomodule 130. Photomodule 130 comprises an LED 132 which is optically coupled to a photosensitive resistance element 134. Photomodule 130 is part of one leg of the bridge network 68. Photomodule 130, series connected resister R51 and parallel coupled resistor R52 form one leg of the bridge. Other legs of the bridge are comprised of resistors R53, R55 and R54. As used herein, the term resistive legs is meant to include other types of elements as well as resistors which may be utilized in conjunction with a bridge network. Conductors 136 and 138 coupled to respective sockets in receptacle 40 connect the excitation signal from the blood pressure monitor to the bridge input. The output of the bridge is coupled to other sockets in receptacle 40 via conductors 140 and 142. Conductor 140 is further coupled via line 144 to five of the pushbutton switches 28–38 of FIG. 1. Switches 28–38 are of the known mechanically interlocking type by which when one pushbutton is engaged, the other switches are automatically disengaged. In this embodiment, the wipers of the switches 28–38 contact the leftmost pole when disengaged and the rightmost pole when engaged. The wipers of switches 30–38 have a common node. The wipers of switches 28–38 are shown positioned in FIG. 4 as would be the case when zero button 30 is engaged. In such case, an external voltage source (+9V) is coupled via OFF switch 28 to the anode of LED 132 in photomodule 130. The current through transistor Q1 is then regulated via the adjustment of potentiometer 66 such that the output of the bridge over lines 138 and 140 would provide a zero indication on the blood pressure monitor under test.

C. The Interconnection Device

Figure 5:
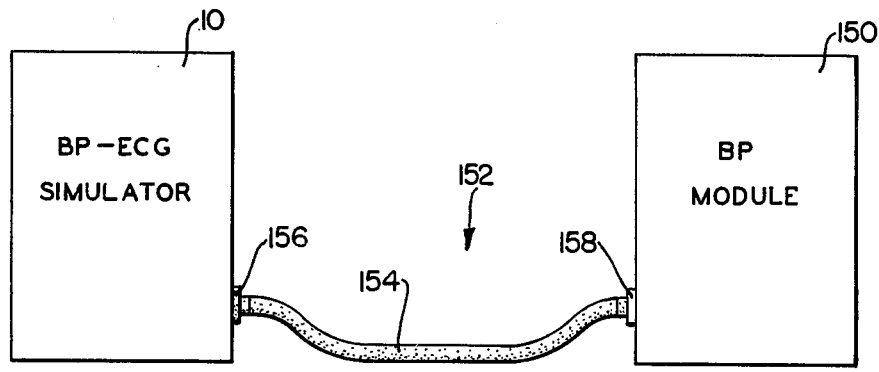
FIG. 5 shows a blood pressure monitor and the simulator device shown in FIG. 1 being coupled together by a cable according to another aspect of this invention.
Figure 6:
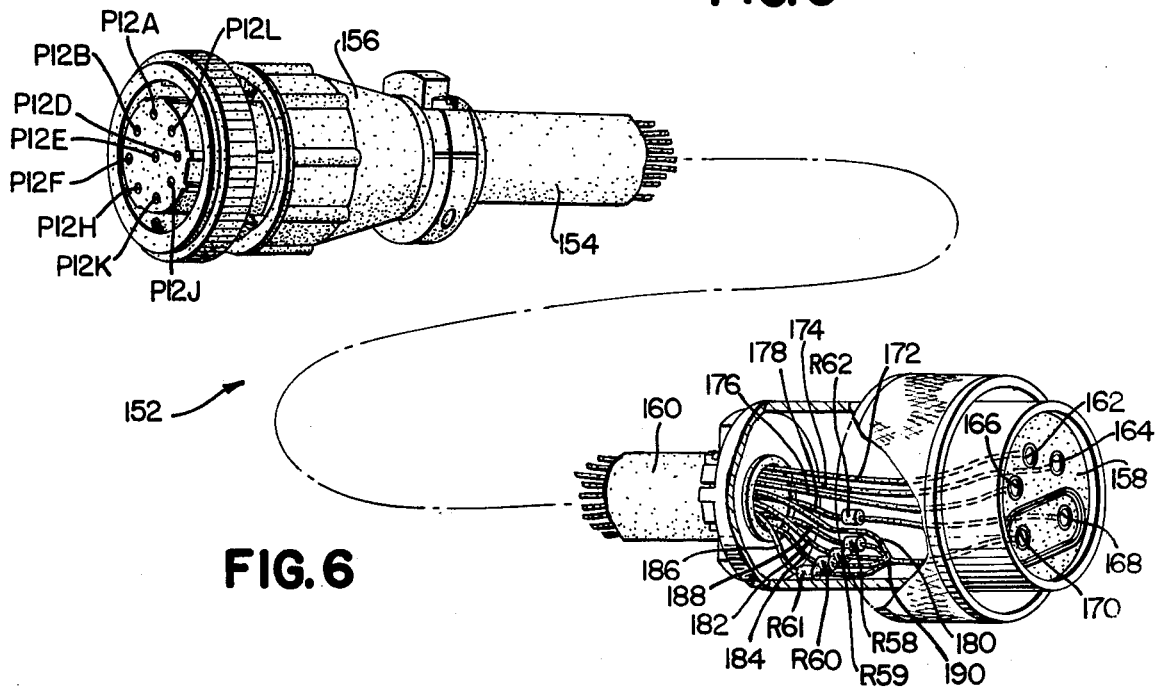
FIG. 6 is a perspective view with parts broken away showing the structure of the cable shown in FIG. 5.
Figure 7:
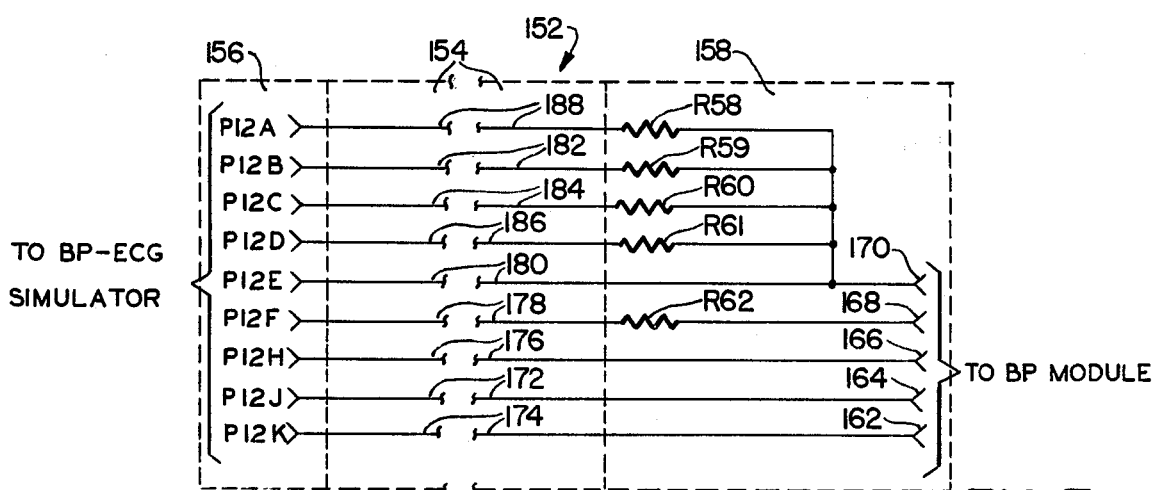
FIG. 7 is an electrical schematic diagram of the cable shown in FIG. 6.

Referring now to FIG. 5, there is shown a typical interconnection between simulator device 10 and a blood pressure monitor 150 which are coupled together via interconnection device 152 according to another aspect of this invention. FIG. 6 shows the graphic details of the interconnection device 152 and FIG. 7 shows the electrical schematic diagram of its respective parts. Device 152 is in the form of a cable 154 having connectors 156 and 158 on each end. Connector 156 may be a commercially available multi-pin plug, such as that manufactured by AMP Corporation. In this embodiment, connector 156 includes nine pins: P12A, P12B, P12C, P12D, P12E, P12F, P12H, P12J and P12K which serve as terminals which mate with sockets in receptacle 40 as shown in FIG. 2. Nine insulated conductors coupled at one end to each of the pins of connector 156 are surrounded by a sheath 160 to form cable 154. Connector 158 in this embodiment has a screw type collar and includes a plurality of sockets 162–170 which are adapted to mate with corresponding pins on the blood pressure monitor 150. Conductors 172 and 174 supply the output of bridge circuit 68 to blood pressure monitor 150. Conductor 176 supplies a ground signal between the two units. Conductors 178–188 supply the internally generated blood pressure monitor excitation signal coupled to sockets 168 and 170 to device 10.

It is a feature of this invention that the interconnection device 152 is specifically designed for the particular blood pressure monitor 150 being utilized. Different types of blood pressure monitors employ different types of excitation signals. For example, such excitation signals can be alternating current, direct current, or pulsed signals which are normally coupled to a transducer (not shown) mounted on a live patient for sensing his blood pressure. Typically such transducers provide a 50 microvolt output per volt of excitation signal when a pressure of one centimeter of mercury is applied to the transducer. In calibrating the blood pressure monitor 150, it is advantageous to provide electrical signals representing static pressure readings which would correspond to 100, 80, 50, and 15 millimeters of mercury pressure applied to the particular transducer normally utilized by monitor 150. Normally, when using such static pressure readings to check the monitor, the blood pressure waveforms are not generated. This is accomplished by removing the biasing voltage, (not shown) to the components in the waveform generator portion of the circuitry, for example by turning switch SW1 (via knob 22) to its OFF position. It is evident, however, that a simulator could not provide static pressure readings which would be compatible with every type of blood pressure monitor since different monitors employ not only different types of excitation signals, but the level of the excitation signal and the sensitivity of the transducer may be different for each monitor. Accordingly, resistors R59-62 are provided to make the simulator and blood pressure monitor compatible regardless of the type of blood pressure monitor being utilized.

Resistor R62 is series connected with conductor 178 to being excitation signal level to one volt at the input of bridge network 68 regardless of the level of the excitation signal utilized by blood pressure monitor 150. For example, if monitor 150 employs a 5 volt excitation signal, resistor R62 is chosen to provide a 4 volt drop across it. Resistors R58-R61 are coupled at one end to conductors 180-186, respectively. The other end of resistors R58-R61 are connected at a common node 190, along with the end of conductor 188. Node 190 is coupled to socket 170 of connector 158. Resistors R58-R61 have different resistance values which are chosen to provide static pressure readings corresponding to 100, 80, 50, and 15 millimeters of mercury to monitor 150 via conductors 172 and 174.

It should be noted that the resistance values of resistor R58-R61 will vary depending upon the particular blood pressure monitor being utilized. When interconnection device 152 is coupled between simulator 10 and monitor 150, resistors R58-R61 can be selectively placed in parallel with bridge resistor R54 depending upon the position of switches 32-38. By way of an example, assume that it is desired to provide a signal equivalent to a static pressure reading of 100 millimeters of mercury. Assume further that monitor 150 employs an excitation signal of 5 volts DC and normally utilizes a transducer having a sensitivity of 50 microvolts per volt of excitation signal for a pressure applied of one centimeter of mercury. Pushbutton switch 32 is activated thereby placing its wiper on the rightmost pole and the wiper of switch 30 on the leftmost pole. Thus, resistor R58 is placed in parallel with resistor R54 of bridge network 68 thereby unbalancing the bridge. With the particular transducer sensitivity and excitation signal being utilized, the output required from the bridge network 68 would be 2.5 millivolts. The value chosen for R58 would be derived from the following equation:

$$R_{cal} = R(\frac{E_{in}-1}{4E_o})$$
$$= 2K\Omega(\frac{1v - 1}{4(2.5mv)})$$
$$= 198K\Omega$$

Where
$E_{in}$ is the voltage applied across the bridge, this being one volt due to the action of resistor R62;
$E_o$ is the output voltage of bridge 68, this being the required 2.5 millivolts;

R=the value of resistor R54 in bridge network 68, this being 2KΩ in this example; and
$R_{cal}$=the resistance value necesaary for R58.
The remaining resistance values of resitors R59-R61 can be chosen in the same manner.

It should be emphasized that the particular types of connectors 156 and 158 can be varied, as can be the location of resistors R58-R62 in the interconnection device 152. In this embodiment, it has been found to be easier to include resistors R58-R62 in the larger type connector utilized for connector 158. However, this is clearly a matter of choice and may be readily varied as is known by a person skilled in the art.

D. Simulator Operation

Figure 8:
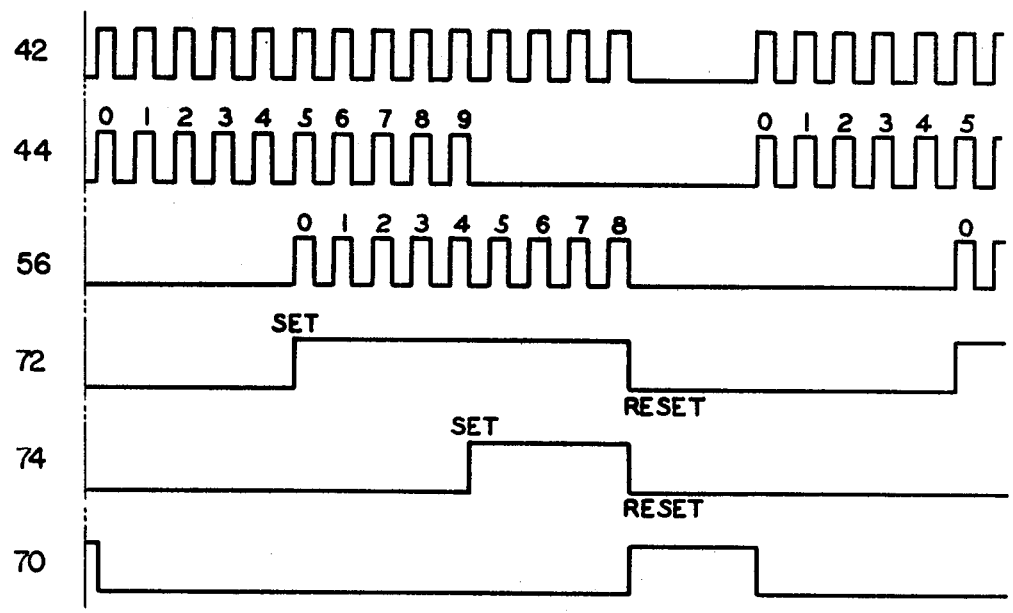
FIG. 8 is a timing circuit illustrating the timing sequence of the circuitry shown in FIG. 3.
Figure 9:
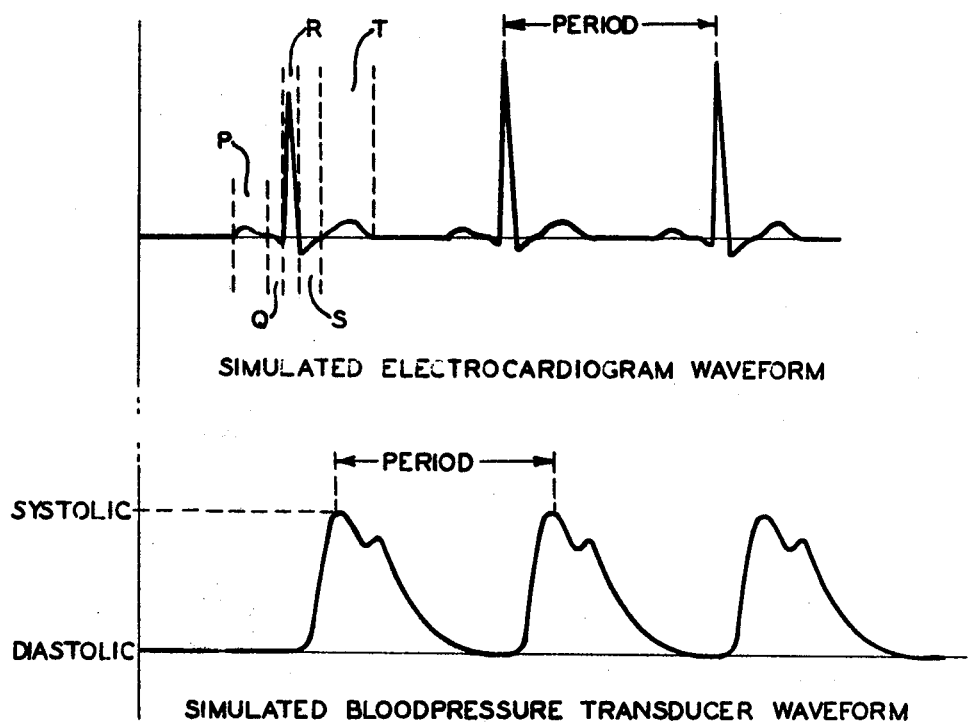
FIG. 9 illustrates the electrocardiographic and blood pressure waveforms supplied by the simulator device of the present invention.

Referring now especially to FIGS. 3, 8 and 9, the operation of the simulator device 10 according to the present invention will now be described. Upon energization of the circuit, clock 42 provides a series of clock pulses as is most clearly shown in FIG. 8. Flip-flops 74 and 76 are initially in their reset stage. Since the enabling input of counter 44 is grounded, it begins to count upon receipt of the clock pulses from clock circuit 42. The stages 0—9 of electrocardiogram counter 44 are sequentially activated as noted by the numerals above the pulses from counter 44 shown in FIG. 8. However, the blood pressure counter 56 is not enabled until the set input of flip-flop 72 receives the rising edge of the pulse emanating from stage 5 of counter 44. When the flip-flop 72 is set, a HIGH signal from flip-flop 72 coupled to the enabling input of counter 56 starts the blood pressure counter 56 to begin counting. Hence, the initiation of the blood pressure waveform is delayed by a predetermined period of time from the beginning of the electrocardiographic waveform. As can be seen most clearly in FIG. 9, since output stage 5 of counter 44 is coupled to the subnetwork in network 46 which creates the S electrocardiographic waveform segment, this causes the respective timed sequence of the two simulated waveforms to represent that which would actually be experienced in monitoring a live patient.

The trailing edge of the output pulse from stage 9 of counter 44 causes flip-flop 74 to change to its set or HIGH level which in turn disables counter 44 by providing the output of flip-flop 74 to the reset input of counter 44. Consequently, decade counter 44 stops counting.

The trailing edge of the pulse from output stage 8 of counter 56 provides a triggering pulse to monostable 70 which in turn provides an output pulse of predetermined width depending upon the position of switch SW1. As noted above, the position of switch SW1 as set by knob 22 of FIG. 1 determines the period of frequency of the respective electrocardiographic and blood pressure waveforms. The HIGH level monostable output pulse disables clock 42 by providing a HIGH signal at the input of inverter 80. Consequently, counter 44 does not count even though flip-flop 74 has been reset by the pulse from monostable 70. Similarly, the monostable output pulse resets flip-flop 72 and associated blood pressure counter 56. Hence for the duration of the HIGH level of the monostable output pulse, both the electrocardiographic and blood pressure waveforms are not provided by the simulator device 10. As also noted above, the position of SW1 via knob 22 selects the frequency of the blood pressure waveform to correspond to 120, 90, or 60 beats per minute.

When the output pulse from monostable 70 returns to its LOW level, the clock circuit 42 is again enabled to provide pulses which drive counter 44 to initiate a second electrocardiographic waveform. However, due to the interaction of the intermediate stage of counter 44 and flip-flop 72, the second blood pressure waveform is not initiated until after the appropriate time has elapsed.

Turn now to the details of the bridge network 68 shown in FIG. 4. When the particular blood pressure monitor 150 is connected to simulator 10 via interconnection device 152, switch SW1 is turned OFF and zero button 30 is engaged by the user to zero the output of the bridge before any blood pressure waveform is generated. Potentiometer 66 is adjusted so that the output of bridge network 68 provides a zero indication on the monitor 150. Static pressure readings of 100, 80, 50, or 15 millimeters of mercury can be provided by pressing buttons 32-38 respectively, as described above. After the waveform generator circuitry is energized via knob 22, the amplitude or systolic level of the blood pressure waveform can be adjusted via potentiometer R62. Hence, the visual indications of the simulated blood pressure waveform on monitor 150 will have a systolic level as determined by potentiometer 62 and a minimum DC or diastolic level as established by the setting of switches 30-38. When the electrical signals emanating from shaping and summing network 58 are applied to the gate of transistor Q1, the conduction between the source and drain regions correspondingly vary as is known in the art. Hence, transistor Q1 provides a variable current source to the photomodule 132, with the current level depending upon the amplitude of the generated blood pressure waveform at the output of potentiometer 62. The intensity of LED 132 proportionally varies pursuant to the current through transistor Q1. Accordingly, the output of bridge 68 over lines 138 and 140 provides the simulated blood signals to monitor 150 since the resistance of photosensitive resistor 134 is dependent upon the light intensity of LED 132.

It is now evident that the interface network of the present invention is compatible with a wide variety of blood pressure monitors regardless of the type of excitation signal employed. The bridge network of the present invention emulates the transducer circuitry that would ordinarily be used with monitor 150 to sense the blood pressure of a live patient. Since the photomodule 130 optically isolates the waveform generator portions of the simulator device 10, the excitation signal from the monitor under test does not effect the waveform generation irrespective of the type of excitation signal employed. Consequently, the simulator device of the present invention can be universally used to check the operability of a variety of blood pressure monitors even though they employ different types of excitation signals.

Therefore, while various aspects of this invention have been described in connection with particular examples thereof as required by the patent statutes, the scope of the invention described herein should not be limited to such examples since modifications will be obvious to one skilled in the art. Hence, the spirit and scope of this invention should be determined in accordance with the following claims.

The embodiments of the invention in which an exclusive property or privilege is claimed are defined as follows:

1. Apparatus for simulating waveforms utilized to check the operability of a remote display device, said remote display device providing an excitation signal which is normally coupled to a transducer for sensing physical characteristics of a live patient, said apparatus comprising:
   (a) generator means for providing electrical signals representing simulated waveforms; and
   (b) an interface circuit for coupling said waveforms to the remote display device, said interface circuit including:
      (1) means defining a bridge network having a plurality of resistive legs, and a variable resistance element in one of said legs coupled to said generator means;
      (2) means for coupling the excitation signal from the remote display device to an input of said bridge network;
      (3) means for coupling an output of said bridge to the remote display device whereby said electrical signals from said generator means cause the resistance of said variable resistance element to correspondingly vary and unbalance the bridge network to provide said simulated waveforms to the remote display device.

2. The apparatus of claim 1 wherein said variable resistance element is a photosensitive device optically coupled to a light emitting diode (LED).

3. The apparatus of claim 2 wherein said interface circuit further comprises:
   transistor means coupled between said generator means and said interface circuit for regulating the amount of current to the LED in response to said electrical signals from the generator means.

4. The apparatus of claim 3 wherein said interface circuit further comprises:
   a source of electrical potential coupled to said transistor means, and a series connected potentiometer for initially adjusting the amount of current to the LED in order to zero the output of the bridge network.

5. The apparatus of claim 4 wherein said transistor means is a field effect transistor having gate, drain and source regions; said gate region being coupled to said generator means, said source region being coupled to said potentiometer, and said drain region being coupled to said source of potential.

6. The apparatus of claim 5 wherein said interface circuit further comprises:
   a plurality of resistance means each having a different resistance value; and
   switch means for selectively coupling one of said resistance means to one leg of the bridge network to thereby unbalance the bridge and change the amplitude of the waveforms to the remote display device.

7. The apparatus of claim 6 wherein said means for coupling comprises:
   a cable for interconnecting said apparatus with said remote display device, said cable having a plurality of conductors therein including first and second conductors for supplying said excitation signal to the bridge network, third and fourth conductors for coupling the bridge output signal to the remote display, and wherein each of said resistance means have one end commonly connected to said first conductor in the cable and their other ends coupled to said switch means.

8. The apparatus of claim 7 wherein the resistance value of said resistance means is chosen to modify the amplitude of the bridge output signal to represent various static pressure readings depending upon the type of the remote display being utilized.

9. The apparatus of claim 8 wherein said plurality of resistance means comprises four in number and wherein the resistance value of the first resistor has a value to modify said bridge output signal to provide a static pressure reading equivalent to 100 millimeters of mercury, the resistance value of said second resistor has a value to modify the bridge output signal to provide a static pressure reading equivalent to 80 millimeters of mercury, the resistance value of said third resistor has a value to modify the bridge output signal to provide a static pressure reading equivalent to 50 millimeters of mercury, and wherein said fourth resistor has a resistance value to modify the bridge output signal to provide a static pressure reading equivalent to 15 millimeters of mercury.

10. The apparatus of claim 9 wherein said second cable conductor includes a serially connected resistor therein to maintain a constant voltage at the input of said bridge network regardless of the level of the excitation signal from the remote display.

11. Apparatus for simulating electrocardiographic and blood pressure waveforms utilized to check the operability of an electrocardiogram machine and a blood pressure monitor, respectively, said apparatus comprising:
   first generator means for providing a simulated electrocardiographic waveform segments;
   second generator means for providing simulated blood pressure waveforms; and
   control means coupled between said first and second generator means for automatically initiating said blood pressure waveform after a predetermined number of the electrocardiographic waveform segments have been generated so that said electrocardiographic and blood pressure waveforms are provided in a time sequence corresponding to waveforms that would ordinarily be supplied by a live patient.

12. The apparatus of claim 11 wherein said first and second waveform generator means includes clock means for providing driving pulses for driving said waveform generator means.

13. The apparatus of claim 11 wherein said first generator means comprises:
   a first counter having a plurality of stages which are sequentially activated by said clock pulses;
   a plurality of analog signal shaping circuits for generating the electrocardiographic waveform segments, each having an input and output, with each input connected to a stage of the counter; and
   summing means connected to the outputs of the analog signal shaping circuits whereby the summing means provides a simulated electrocardiographic waveform at its output.

14. The apparatus of claim 13 wherein said second generator means comprises;
   a second counter having a plurality of stages which are sequentially activated by said clock pulses;
   a plurality of analog signal shaping circuits each having an input and output, with each input connected to a stage of said second counter; and
   second summing means connected to the outputs of said analog signal shaping circuits whereby the second summing means provides a simulated blood pressure waveform at its output.

15. The apparatus of claim 14 wherein said control means further comprises:
   a first flip-flop having set and reset inputs, and an output;
   means for coupling the output of the first flip-flop to an enabling input of said second counter; and
   means for coupling the set input of said first flip-flop to an intermediate stage of said first counter thereby delaying the beginning of the blood pressure waveform with respect to the beginning of said electrocardiographic waveform.

16. The apparatus of claim 15 wherein said output stages of the first counter are connected to analog signal shaping circuits for providing P, Q, R, S, and T electrocardiographic waveform segments.

17. The apparatus of claim 16 wherein said intermediate stage of the first counter is that stage which is coupled to the analog signal shaping circuit for providing the S electrocardiographic waveform segment.

18. The apparatus of claim 17 which further comprises:
   a second flip-flop having set and reset inputs, and an output;
   means for coupling the last stage of said first counter to the set input of said second flip-flop;
   means for coupling the output of said second flip-flop to a disabling input of said first counter;
   monostable means for providing an output pulse of a given width upon receipt of a trigger pulse at its input;
   means coupling the last stage of said second counter to the input of said monostable means to provide the trigger pulse when said last stage of the second counter is activated; and
   means for coupling the output pulse of said monostable means to the reset input of said first flip-flop, the reset input of said second flip-flop, a disabling input of said clock means, and to a disabling input of said second counter means whereby to regulate the periods between the electrocardiographic and blood pressure waveforms.

19. The apparatus of claim 18 wherein said monostable means further comprises:
   means for adjusting the width of the output pulse from said monostable means to thereby change the periods of said electrocardiographic and said blood pressure waveforms.

20. An interconnection device for interconnecting a blood pressure monitor and a blood pressure waveform simulator device, with said blood pressure monitor providing an excitation signal and including means for receiving an input signal, said interconnecting device comprising:
   a cable having a plurality of conductors;
   a first connector means on one end of said cable having terminals for coupling said conductors to the blood pressure monitor;
   a second connector means at the other end of the cable having terminals for coupling said conductors to said simulator device; and
   a plurality of resistors having first and second end portions, the first end portions of the resistors being commonly connected to one of the conductors for supplying the excitation signal from blood pressure monitor to the simulator device, the other end portions of the resistors each being coupled to a separate terminal in one of said connectors to provide alternative conductive paths from the blood pressure monitor to said simulator device.

21. The device of claim 20 wherein said plurality of conductors comprise at least four in number in which the first and second conductors supply said excitation signal to the simulator device, and in which third and fourth conductors couple the output signals of the simulator device to said blood pressure monitor.

22. The device of claim 21 which further comprises: an additional resistor serially connected with said first conductor, said resistor having a resistance value such that a portion of said excitation signal from the blood pressure monitor is dropped thereacross.

23. The device of claim 22 wherein said plurality of resistors each have different resistance values which are chosen to provide a plurality of different static pressure readings from said simulator device to said blood pressure monitor.

24. The device of claim 20 wherein said second connector means is adapted to be coupled to an interface network in said simulator device, said interface network including a resistive bridge network having a plurality of resistive legs.

25. The device of claim 24 wherein said plurality of resistors comprises four in number, and wherein when coupled to one of the resistive legs of said interface network the first resistor conditions said simulator device to provide a static pressure reading corresponding to 100 millimeters of mercury, said second resistor conditions said simulator device to provide a static pressure reading of 80 millimeters of mercury, said third resistor conditions said simulator device to provide a static pressure reading of 50 millimeters of mercury, and said fourth resistor conditions said simulator device to provide a static pressure reading of 15 millimeters of mercury.

* * * * *